(12) United States Patent
Cui et al.

(10) Patent No.: US 11,845,809 B2
(45) Date of Patent: Dec. 19, 2023

(54) MALEATE OF SCY-635 AND USES THEREOF IN MEDICINE

(71) Applicant: WATERSTONE PHARMACEUTICALS(WUHAN) CO., LTD., Hubei (CN)

(72) Inventors: Jian Cui, Hubei (CN); Yao Yu, Hubei (CN); Minglong Hu, Hubei (CN)

(73) Assignee: WATERSTONE PHARMACEUTICALS(WUHAN) CO., LTD., Hubei (CN)

( * ) Notice: Subject to any disclaimer, the term of this patent is extended or adjusted under 35 U.S.C. 154(b) by 445 days.

(21) Appl. No.: 17/413,054

(22) PCT Filed: Dec. 14, 2018

(86) PCT No.: PCT/CN2018/121300
§ 371 (c)(1),
(2) Date: Jun. 11, 2021

(87) PCT Pub. No.: WO2020/118714
PCT Pub. Date: Jun. 18, 2020

(65) Prior Publication Data
US 2022/0024984 A1    Jan. 27, 2022

(51) Int. Cl.
*C07K 7/64* (2006.01)
*A61P 31/12* (2006.01)

(52) U.S. Cl.
CPC .............. *C07K 7/645* (2013.01); *A61P 31/12* (2018.01)

(58) Field of Classification Search
None
See application file for complete search history.

(56) References Cited

U.S. PATENT DOCUMENTS 5,994,299 A    11/1999    Barriere et al.

FOREIGN PATENT DOCUMENTS

| WO | 2011072370 A1 | 6/2011 |
|---|---|---|
| WO | 2010080878 A1 | 7/2020 |

OTHER PUBLICATIONS

Hopkins et al., "The Cyclophilin Inhibitor SCY-635 Disrupts Hepatitis C Virus NS5A-Cyclophilin A Complexes," Antimicrobial Agents and Chemotherapy, 2012, vol. 56, No. 7.
EPO, Extended European Search Report for EP Application No. 18943221.4, dated Jul. 11, 2022.
WIPO, International Search Report for PCT/CN2018/121300, dated Sep. 18, 2019.

*Primary Examiner* — Christina Bradley
(74) *Attorney, Agent, or Firm* — Hodgson Russ LLP (57) ABSTRACT

The present invention relates to a salt of a compound of formula (I) and uses thereof in medicine. Specifically, it relates to maleate of compound of formula (I) and pharmaceutically compositions thereof. Furthermore, the invention relates to the uses of maleate herein and pharmaceutically compositions thereof disclosed herein in the manufacture of a medicament, especially in the manufacture of a medicament for preventing, managing, treating or lessening hepatitis C virus (HCV) infection.

(I)

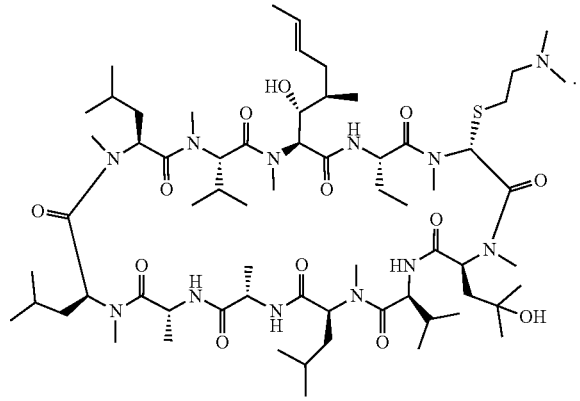

5 Claims, 5 Drawing Sheets

MALEATE OF SCY-635 AND USES THEREOF IN MEDICINE

CROSS REFERENCE TO RELATED APPLICATIONS

This application is a U.S. national phase application based on the International Application No. PCT/CN2018/121300 filed on Dec. 14, 2018, the entire contents of which is incorporated by reference herein.

FIELD OF THE DISCLOSURE

The present invention belongs to the field of medicine. Specifically, it relates to maleate of (3S,6S,9S,12R,15S,18S, 21 S,24S,27R,30S,33 S)-27-((2-(dimethylamino)ethyl) thio)-30-ethyl-33-((1R,2R,E)-1-hydroxy-2-methylhex-4-en-1-yl)-24-(2-hydroxy-2-methylpropyl)-6,9,18-triisobutyl-3, 21-diisopropyl-1,4,7,10,12,15,19,25,28-nonamethyl-1,4,7, 10,13,16,19,22,25,28,31-undecaazacyc lotritriacontan-2,5, 8,11,14,17,20,23,26,29,32-undecaone (I) (SCY-635), and pharmaceutically composition thereof. Furthermore, it relates to the uses of salt and pharmaceutically compositions thereof in the manufacture of a medicament, especially in the manufacture of a medicament for preventing, managing, treating or lessening chronic hepatitis C and hepatitis C infection in a patient.

BACKGROUND OF THE INVENTION

SCY-635 (the compound of formula (I)) is a novel non-immunosuppressive cyclosporine-based analog that exhibits potent suppression of hepatitis C virus (HCV) replication in vitro. SCY-635 inhibited the peptidyl prolyl isomerase activity of cyclophilin A at nanomolar concentrations but showed no detectable inhibition of calcineurin phosphatase activity at concentrations up to 2 µM. Metabolic studies indicated that SCY-635 did not induce the major cytochrome P450 enzymes 1A2, 2B6, and 3A4. SCY-635 was a weak inhibitor and a poor substrate for P-glycoprotein. Functional assays with stimulated Jurkat cells and stimulated human peripheral blood mononuclear cells indicated that SCY-635 is a weaker inhibitor of interleukin-2 secretion than cyclosporine. A series of two-drug combination studies was performed in vitro. SCY-635 exhibited synergistic antiviral activity with alpha interferon 2b and additive antiviral activity with ribavirin. SCY-635 was shown to be orally bioavailable in multiple animal species and produced blood and liver concentrations of parent drug that exceeded the 50% effective dose determined in the bicistronic con1b-derived replicon assay. These results suggest that SCY-635 warrants further investigation as a novel therapeutic agent for the treatment of individuals who are chronically infected with HCV.

The inventors found that the compound was a solid with poor solubility, which had poor bioavailability, and brought lots of inconvenience for later development of preparations. Different salts of a pharmaceutically active ingredient may have different properties. The change of properties of different salts can provide improved formulations, such as improvement of dissolution rate or stability and shelf life. The final dosage form can also be improved due to changes in properties caused by different salts, for example if such changes can increase exposure, bioavailability or prolong half-life. Therefore, salts research on compounds can provide a basis for the subsequent pharmaceutical use of the said compounds.

SUMMARY OF THE DISCLOSURE

In order to find a better salt of the compound of formula (I) with better pharmaceutical properties, the inventors have only obtained one salt of the compound of formula (I) through many experimental studies. The said salt of the compound of formula (I), properties of drug metabolism and the physicochemical properties thereof, and the like, have been researched, and it has been found that the salt have good water solubility, stability and pharmacokinetic properties, and the like.

The present invention relates to maleate of (3S,6S,9S, 12R,15S,18S,21S,24S,27R,30S,33S)-27-((2-(dimethylamino)ethyl)thio)-30-ethyl-33-((1R,2R,E)-1-hydroxy-2-methylhex-4-en-1-yl)-24-(2-hydroxy-2-methylpropyl)-6,9,18-triisobutyl-3,21-diisopropyl-1,4,7,10,12,15,19,25,28-nonamethyl-1,4,7,10,13,16,19,22,25,28,31-undecaazacyclotritriacontan-2,5,8,11,14,17,20,23,26,29,32-undecaone (I) (SCY-635), and pharmaceutically compositions thereof.

Furthermore, it relates to the uses of maleate and pharmaceutical composition thereof in the manufacture of a medicament, especially in the manufacture of a medicament for preventing, managing, treating or lessening hepatitis C infection.

In one aspect, provided herein is a salt of a compound of formula (I), wherein the salt is maleate.

(I)

The inventors did a lot of experiments, including screening a variety of salts and screening a variety of solvents, and finally found that only the said salt can make the compound of formula (I) to be a more stable salt. According to the examples of present disclosure, the said maleate of the compound of formula (I) have better water solubility, stability and pharmacokinetic properties than the compound of formula (I) itself.

In some embodiments, a mole ratio of the compound of formula (I) to maleic acid in the maleate of the compound of formula (I) is from 1:0.9 to 1:1.2. The inventors found that the compound of formula (I) has a tertiary amine, which can be acceptable for a maleate.

In some embodiments, a mole ratio of the compound of formula (I) to maleic acid in the maleate of the compound of formula (I) is 1:1.

In another aspect, provided herein is a pharmaceutical composition comprising the said salt of the compound of formula (I) above, and a pharmaceutically acceptable excipient. According to the examples of present disclosure, the said pharmaceutical composition is more stable and can be used in preventing, managing, treating or lessening chronic hepatitis C and hepatitis C infection in a patient.

In another aspect, provided herein is use of the salt said above, or the pharmaceutical composition said above, in the manufacture a medicament for preventing, managing, treating or lessening chronic hepatitis C and hepatitis C infection in a patient.

In another aspect, provided herein is a method of preventing, managing, treating or lessening chronic hepatitis C and hepatitis C infection, comprising administering to a patent in need of such treatment a therapeutically effective amount of the salt said above, or the pharmaceutical composition said above.

In another aspect, provided herein is the salt said above, or the pharmaceutical composition said above, for use in preventing, managing, treating or lessening chronic hepatitis C and hepatitis C infection in a patient.

DESCRIPTION OF THE DISCLOSURE

The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

In the invention, the compound of formula (I), the maleate thereof may contain solvent. In some embodiments, the solvent contained herein contributes to the internal stability of the maleate thereof. Common solvents include, water, ethanol, methanol, isopropanol, acetone, isopropyl ether, ethyl ether, isopropyl acetate, n-heptane, tetrahydrofuran, dichloromethane, ethyl acetate, etc. The above-mentioned the maleate of the compound represented by formula (I) according to the present invention, it is intended to be included within the scope of the present invention.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety. Although many methods and materials similar or equivalent to those described herein could be used in the practice or test of the present invention, the preferred methods, equipments and materials are described in the invention.

Definitions and General Terminology

The term "comprise" is an open expression, it means comprising the contents disclosed herein, but don't exclude other contents.

As described herein, "room temperature (RT)" refers to a temperature from about 10° C. to about 40° C. In some embodiments, "room temperature" refers to a temperature from about 20° C. to about 30° C.; in other embodiments, "room temperature" refers to a temperature from about 25° C. to about 30° C.

The term as used herein, "pharmaceutically acceptable" means a substance is acceptable from the standpoint of toxicology for pharmaceutical applications and does not adversely interact with active ingredients.

The term as used herein, "polycrystalline form" or "polymorphism" is defined as the possibility that there are at least two different crystalline arrangements for the same chemical molecule. "Amorphism" or "amorphous form" refers to substance forming by particle (such as molecule, atom, ion) arranged in no periodic in three-dimensional space, which is characterized by a diffused X-ray powder diffraction pattern with no sharp peaks. Amorphism is a special physical form of solid substance, the ordered structural characteristics in a part of amorphous substance imply there are innumerable links between amorphous substance and crystal substance. Amorphous form of a substance can be obtained by a number of methods as known in the art. These methods include, but are not limited to, rapid freezing method, anti-solvent flocculence, ball-milling method, spray drying method, freeze-drying method, wet granulating method and solid dispersion technique, and the like.

The term "solvent", as used herein, means a substance, typically a liquid, that is capable of completely or partially dissolving another substance, typically a solid. Solvents for the practice of the invention include, but are not limited to, water, acetic acid, ethyl ether, isopropyl ether, petroleum ether, isopropyl acetate, methyl tert-butyl ether, n-heptane, acetone, acetonitrile, benzene, chloroform, tetrachloromethane, dichloromethane, dimethyl sulfoxide, 1,4-dioxane, ethanol, ethyl acetate, n-butanol, tert-butanol, N,N-dimethylacetamide, N,N-dimethylformamide, formamide, formic acid, hexane, isopropanol, methanol, methyl ethyl ketone, 1-methyl-2-pyrrolidone, mesitylene, nitromethane, polyethylene glycol, n-propanol, 2-acetone, pyridine, tetrahydrofuran, toluene, xylene, mixtures thereof, etc.

The term "equivalent" or "eq.", is the equivalent amount of other raw materials needed according to the chemical reaction equivalent relationship, wherein the basic raw material is used as the base (1 equivalent) in each step.

Unless otherwise stated, structures depicted herein are also meant to include all isomeric (e.g., enantiomeric, diastereomeric, and geometric (or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric mixtures of the present compounds are within the scope disclosed herein.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley&Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process.

As used herein, "patient" refers to a human (including adults and children) or other animal. In one embodiment, "patient" refers to a human.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment, "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

The Pharmaceutical Compostions Comprising the Compound, Salt of the Invention

As described above, the pharmaceutically acceptable compositions disclosed herein further comprise a pharmaceutically acceptable excipient, which, as used herein, includes any and all solvents, solid excipients, diluent, adhesives, disintegrant or other liquid vehicle, dispersion, flavoring agents or suspension aids, surface active agents, isotonic agents, thickening or emulsifying agents, preservatives, solid binders, glidants, lubricants and the like, as suited to the particular dosage form desired. As the following described: Troy et al., Remington: The Science and Practice of Pharmacy, 21st ed., 2005, Lippincott Williams & Wilkins, Philadelphia, and Swarbrick et al., Encyclopedia of Pharmaceutical Technology, eds. 1988-1999, Marcel Dekker, New York, both of which are herein incorporated by reference in their entireties, discloses various excipients used in formulating pharmaceutically acceptable compositions and known techniques for the preparation thereof. Except insofar as any conventional excipients incompatible with the compounds disclosed herein, such as by producing any undesirable biological effect or otherwise interacting in a deleterious manner with any other components of the pharmaceutically acceptable composition, its use is contemplated to be within the scope of this invention.

Some non-limiting examples of materials which can serve as pharmaceutically acceptable excipients include ion exchangers; aluminium; aluminum stearate; lecithin; serum proteins such as human serum albumin; buffer substances such as phosphates; glycine; sorbic acid; potassium sorbate; partial glyceride mixtures of saturated vegetable fatty acids; water; salts or electrolytes such as protamine sulfate, disodium hydrogen phosphate, potassium hydrogen phosphate, sodium chloride and zinc salts; colloidal silica; magnesium trisilicate; polyvinyl pyrrolidone; polyacrylates; waxes; polyethylene-polyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants.

The compound, salt, or pharmaceutical compositions disclosed herein are suitable for the treatment of acute and chronic viral infections of infectious hepatitis, particularly can inhibit hepatitis C virus (HCV) effectively, and are suitable for treating or lessening diseases induced by viruses in a patient, especially chronic HCV infections.

The compound, salt or pharmaceutical composition disclosed herein may be administered in any of the following routes: orally, inhaled by spray, locally, rectally, nasally, vaginally, parenterally such as subcutaneous, intravenous, intramuscular, intraperitoneal, intrathecal, intraventricular, intrasternal, or intracranial injection or infusion, or administered with the aid of an explanted reservoir. Administration routes by orally, intramuscular, intraperitoneal or intravenous injection are preferred.

The compound, salt or pharmaceutically acceptable composition thereof may be administered in a unit dosage form. The dosage form may be in a liquid form, or a solid form. The liquid form includes true solutions, colloids, particulates, suspensions. Other dosage forms include tablets, capsules, dropping pills, aerosols, pills, powders, solutions, suspensions, emulsions, granules, suppositories, freeze-dried powder injection, and the like.

Oral tablets and capsules may comprise excipients, e.g., binders, such as syrup, arabic gum, sorbitol, tragacanth or polyvinylpyrrolidone; fillers, such as lactose, sucrose, corn starch, calcium phosphate, sorbitol, glycine; lubricants such as magnesium stearate, talc, polyethylene glycol, silica; disintegrating agents, such as potato starch; or acceptable moisturizing agents such as sodium lauryl sulfate. Tablets may be coated by using known methods in pharmaceutics.

Oral solution may be made as a suspension of water and oil, a solution, an emulsion, syrup or an elixir, or made as a dried product to which water or other suitable medium is added before use. This liquid preparation may comprise conventional additives, e.g., suspending agents, sorbitol, cellulose methyl ether, glucose syrup, gel, hydroxyethyl cellulose, carboxymethyl cellulose, aluminum stearate gel, hydrogenated edible greases; emulsifying agents such as lecithin, sorbitan monoleate, arabic gum; or non-aqueous carriers (possibly including edible oil), such as almond oil, grease such as glycerin, ethylene glycol, or ethanol; antiseptics such as methyl or propyl p-hydroxybenzoate, sorbic acid. If desired, a flavoring agent or a colorant may be added.

Suppositories may comprise a conventional suppository base, such as cocoa butter or other glyceride.

For parenteral administration, the liquid dosage form is usually made from the compound and a sterilized carrier. The preferred carrier is water. According to the difference of selected carrier and drug concentration, the compound can be either dissolved in the carrier or made into a supernatant solution. When being made into a solution for injection, the compound is firstly dissolved in water, and then filtered and sterilized before being packaged into a sealed bottle or an ampoule.

For application topically to the skin, the salt of the compound disclosed herein may be made into a suitable form of ointments, lotions or creams, wherein the active ingredient is suspended or dissolved in one or more carrier(s). Wherein carriers used for an ointment preparation include, but are not limited to: mineral oil, liquid vaseline, white vaseline, propylene glycol, polyoxyethylene, polyoxypropylene, emulsified wax and water; carriers used for a lotion and a cream include, but are not limited to: mineral oil, sorbitan monostearate, Tween 60, cetyl ester wax, hexadecylene aromatic alcohol, 2-octyl dodecanol, benzyl alcohol and water.

The pharmaceutical composition provided herein further comprises anti-HCV drugs, and the anti-HCV drug is an HCV polymerase inhibitor, immunomodulator or interferon.

Use of the Compound, Salt or Pharmaceutical Composition of the Invention

In another aspect, provided herein is use of the compound, salt or pharmaceutical composition disclosed herein in the manufacture of a medicament for preventing, managing, treating or lessening HCV diseases in a patient, comprising administering a pharmaceutically acceptable effective amount to a patient. The HCV disease is a hepatic disease caused by hepatitis C virus infection or hepatitis C infection, including acute hepatitis, chronic hepatitis, cirrhosis and hepatocellular carcinoma. The symptoms of acute hepatitis C virus infection may be asymptomatic or manifested as acute hepatitis symptoms. A patient with chronic virus infection suffers an active disease, which can progress to cirrhosis and liver cancer.

An "effective amount", "a therapeutically effective amount" or "effective dose" of the compound, salt, crystalline form, complex or pharmaceutically acceptable composition disclosed herein is an amount that is effective in treating or lessening the severity of one or more of the aforementioned disorders. The complex and pharmaceutically acceptable compositions are effective administered in a fairly wide dose range. For example, the daily dose is from about 0.1 mg to 1000 mg per person, the compounds or pharmaceutically acceptable compositions can be administered in a single dose or in several divided doses a day. The salts and compositions, according to the method disclosed herein, may be administered using any amount and any route of administration which is effective for treating or lessening the severity of the disorder or disease. The exact amount required will vary from subject to subject, depending on the species, age, and general condition of the subject, the severity of the infection, the particular agent, its mode of administration, and the like. The compound, salt or pharmaceutical composition disclosed herein can also be administered with one or more other therapeutic agents as discussed above.

DESCRIPTION OF THE PREFERRED EMBODIMENTS

The embodiment of the present invention is described in detail, and an example of the embodiment is shown in the drawing. The embodiments described below by reference to the drawings are illustrative and are intended to be used to interpret the present invention and cannot be understood as a limitation to the present invention.

General Preparation and Detection Methods

The features and advantages of the present invention will become apparent to those of ordinary skilled in the art upon reading the following detailed description. It should be understood that certain features of the invention, which are, for clarity, described in the context of separate embodiments, can also be provided in combination in a single embodiment. Conversely, various features of the invention which are, for brevity, described in the context of a single embodiment, can also be provided in any suitable subcombination. The following examples disclosed herein are presented to further describe the invention. However, these examples should not be used to limit the scope or spirit of the invention to the specific steps described therein.

In the examples described below, unless otherwise indicated all temperatures are set forth in degrees Celsius (° C.). Reagents were purchased from commercial suppliers such as Aladdin, Sinopharm Chemical Reagent and Adamas-beta, and were used without further purification unless otherwise indicated. Common solvents were purchased from commercial suppliers such as Sinopharm Chemical Reagent and Shanghai Titan Scientific.

$^1$H NMR spectra were recorded by a Bruker Avance 400 spectrometer or Bruker Avance III HD 600 spectrometer, using CDCl$_3$, DMSO-d6, CD$_3$OD or acetone-d6 (reported in ppm) as solvent, and using TMS (0 ppm) or chloroform (7.26 ppm) as the reference standard. When peak multiplicities are reported, the following abbreviations are used: s (singlet), s, s (singlet, singlet), d (doublet), t (triplet), m (multiplet), br (broadened), dd (doublet of doublets), ddd (doublet of doublet of doublets), dt (doublet of triplets), ddt (doublet of doublet of triplets), td (triplet of doublets), br.s (broadened singlet). Coupling constants J, when given, were reported in Hertz (Hz).

"XRPD" refers to X-ray powder diffraction. Some informations such as change in crystalline form, crystallinity, crystal structure state, etc., can be obtained through detection of X-ray powder diffraction (XRPD) which is a common method used for identifying crystalline form. The term "X-ray powder diffraction pattern" or "XRPD pattern" refers to the experimentally observed diffractogram or parameters derived therefrom. The X-ray powder diffraction (XRPD) is characterized by the peak position (abscissa) and the peak intensity (ordinate). The peak position of XRPD pattern mainly depends on the crystal structure, which is relatively insensitive to experimental details, and the relative peak height depends on many factors related to sample preparation and the geometry of the instrument. Thus, in some embodiments, the crystalline form disclosed herein is characterized by an X-ray powder diffraction pattern having some peaks in certain positions, which is substantially the same as the XRPD pattern provided in appended figures of the present invention.

Agilent 1100 HPLC was utilized to measure purity, method listed in table 1.

TABLE 1

| HPLC method for purity test | | |
|---|---|---|
| HPLC | Agilent 1100 with DAD detector | |
| Column | Waters Xbridge Shield RP C18 110A, 150 × 4.6 mm, 5 µm | |
| Mobile phase | A: 0.1% TFA in H$_2$O; B: 0.1% TFA in acetonitrile | |
| Gradient table | Time (min) | % B |
| | 0.0 | 20 |
| | 3.0 | 35 |
| | 25.0 | 45 |
| | 35.0 | 95 |
| | 37.0 | 95 |
| | 37.1 | 20 |
| | 40.0 | 20 |
| Run time | 40.0 min | |
| Post time | 0.0 min | |
| Flow rate | 1.0 mL/min | |

TABLE 1-continued

| HPLC method for purity test | |
|---|---|
| Injection volume | 5 µL |
| Detector wavelength | UV at 205 nm, reference 500 nm |
| Column temperature | 40° C. |
| Sampler temperature | RT |
| Diluent | Acetonitrile |

IC method for counter-ion content measurement to determine stoichiometric ratio was listed in Table 2 below.

TABLE 2

| IC method for counter-ion content measurement | |
|---|---|
| Parameters | Settings |
| Column | IonPac AS18 Analytical Column (4 × 250 mm) |
| Mobile Phase | 25mM NaOH |
| Injection volume | 25 µL |
| Flow rate | 1.0 mL/min |
| Cell temperature | 35° C. |
| Column temperature | 35° C. |
| Current | 80 mA |
| Run Time | 28 min |

The following examples disclosed herein are presented to further describe the invention. However, these examples should not be used to limit the scope of the invention.

The compound of formula (I) (SCY-635) can be prepared refer to the method described in any reasonable synthetic methods, or through commercial purchase.

Example 1: Salt Screening

Twenty-four salt formers and five solvent systems were used in the initial salt screening.

About 15 mg of freebase was dispersed in selected solvent in a glass vial and corresponding salt former was added with a molar charge ratio of 1:1 (for HCl/freebase, two ratios of both 1:1 and 2:1 were used). The mixtures of freebase and acid were stirred at 5° C. for about 4 days after stirring at RT for 4 hours. Clear solutions obtained after stirring were transferred to anti-solvent addition or slow evaporation at RT, in order to maximize the possibility of identifying as many crystalline hits as possible. Resulted solids were isolated and analyzed by XRPD. As summarized in Table 3, no new crystalline solid was isolated. And as showed in Table 3, non mucic acid salt was obtained. That is to say, the salt forming property of compound I has selectivity.

TABLE 3

| Summary of initial salt screening | | | | | | |
|---|---|---|---|---|---|---|
| | | Solvent | | | | |
| | Salt Form (acid:FB) | EtOAc | Acetone | ACN | THF | EtOH/H2O (19:1, v:v) |
| 1 | HCl (1:1) | Amorphous | Amorphous | Amorphous | Amorphous | Amorphous |
| 2 | HCl (2:1) | Amorphous | Amorphous | Amorphous | Amorphous | Gel |
| 3 | H$_2$SO$_4$ | Amorphous* | Amorphous | Amorphous | Amorphous | Amorphous |
| 4 | H$_3$PO$_4$ | Amorphous* | Amorphous | Amorphous | Amorphous | Amorphous |
| 5 | Acetic acid | Gel | Amorphous | Amorphous | Amorphous | Amorphous |

TABLE 3-continued

Summary of initial salt screening

| | Salt Form (acid:FB) | Solvent | | | | |
|---|---|---|---|---|---|---|
| | | EtOAc | Acetone | ACN | THF | EtOH/H2O (19:1, v:v) |
| 6 | Maleic acid | Amorphous maleate* | Amorphous | Amorphous | Amorphous | Amorphous |
| 7 | Fumaric acid | Amorphous* | Amorphous | Amorphous | Amorphous | Amorphous |
| 8 | Succinic acid | Amorphous | Amorphous | Amorphous | Amorphous | Amorphous |
| 9 | Malic acid | Amorphous* | Amorphous | Amorphous | Amorphous | Gel |
| 10 | L-tartaric acid | Amorphous* | Amorphous | Amorphous | Amorphous | Amorphous |
| 11 | Adipic acid | Amorphous | Amorphous | Amorphous | Amorphous | Amorphous |
| 12 | Hippuric acid | Weakly crystalline | Amorphous | Gel | Weakly crystalline | Amorphous |
| 13 | Citric acid | Amorphous* | Amorphous | Amorphous | Amorphous | Amorphous |
| 14 | Glycolic acid | Amorphous | Weakly crystalline | Amorphous | Amorphous | Gel |
| 15 | Nicotinic acid | Amorphous | Amorphous | Amorphous | Amorphous | Amorphous |
| 16 | Benzoic acid | Amorphous | Amorphous | Amorphous | Amorphous | Amorphous |
| 17 | Oxalic acid | Amorphous* | Amorphous | Amorphous | Amorphous | Amorphous |
| 18 | Gentisic acid | Amorphous* | Amorphous | Amorphous | Amorphous | Amorphous |
| 19 | Ethane-disulfonic acid | Weakly crystalline** | Amorphous | Amorphous | Amorphous** | Amorphous |
| 20 | Toluene-sulfonic acid | Weakly crystalline* | Amorphous | Amorphous | Amorphous | Amorphous |
| 21 | Mucic acid | Mucic acid** | Mucic acid** | Mucic acid** | Mucic acid** | Mucic acid** |
| 22 | L-lactic acid | Amorphous | Amorphous | Amorphous | Amorphous | Amorphous |
| 23 | 1,5-Naphthalene disulfonic acid | Amorphous napadisylate* | Amorphous | Amorphous | Amorphous | Amorphous |
| 24 | Nicotinamide | Amorphous* | Amorphous | Amorphous | Amorphous | Gel |
| 25 | Malonic acid | Amorphous* | Amorphous | Amorphous | Amorphous | Amorphous |

*Solids were obtained by anti-solvent addition.
**Solids were obtained via slurry directly.
Weakly crystalline: minor diffraction peaks with low intensity observed from isolated solids. The others: slow evaporation at RT.

Example 2: Sulfate and Phosphate

About 50 mg of amorphous sulfate and phosphate were prepared and the preparation procedures were summarized in Table 4. A low HPLC purity of 77% was observed for sulfate, as shown in Table 5 and FIG. 3. For phosphate, a high purity was observed (Table 6 and FIG. 2).

TABLE 4

Preparation procedures of sulfate and phosphate

| Salt | Preparation Procedures |
|---|---|
| Sulfate | 1. Dissolve 50 mg of freebase in 0.2 mL of EtOAc in a 3-mL of glass vial and magnetically stirring at RT.<br>2. Dissolve 3.14 µL of concentrated $H_2SO_4$ (18 mol/L) in 0.25 mL of EtOAc.<br>3. Add diluted $H_2SO_4$ solution in step 2 into the 3-mL of glass vial and stir the mixture at 5° C. for two days.<br>4. Gel-like solid is isolated and dried at 50° C. for about 5 min. |
| Phosphate | 1. Dissolve 50 mg of freebase in 0.2 mL of EtOAc in a 3-mL of glass vial and magnetically stirring at RT.<br>2. Dissolve 2.6 µL of concentrated $H_3PO_4$ (14.6 mol/L) in 0.2 mL of EtOAc.<br>3. Add diluted acid in step 2 into the 3-mL of glass vial and stir the mixture at 5° C. for two days with 0.3 mL of n-heptane was added.<br>4. Gel-like solid is isolated and dried at 50° C. for about 5 min. |

TABLE 5

HPLC impurity table of sulfate

| # Peak | Time (min) | RRT | Area (%) |
|---|---|---|---|
| 1 | 8.86 | 0.43 | 1.39 |
| 2 | 11.68 | 0.56 | 17.19 |
| 3 | 13.48 | 0.65 | 4.30 |
| 4 | 20.71 | 1.00 | 77.13 |

TABLE 6

HPLC impurity table of phosphate

| # Peak | Time (min) | RRT | Area (%) |
|---|---|---|---|
| 1 | 20.68 | 1.00 | 100.00 |

Example 3: Maleate

Figure 2:
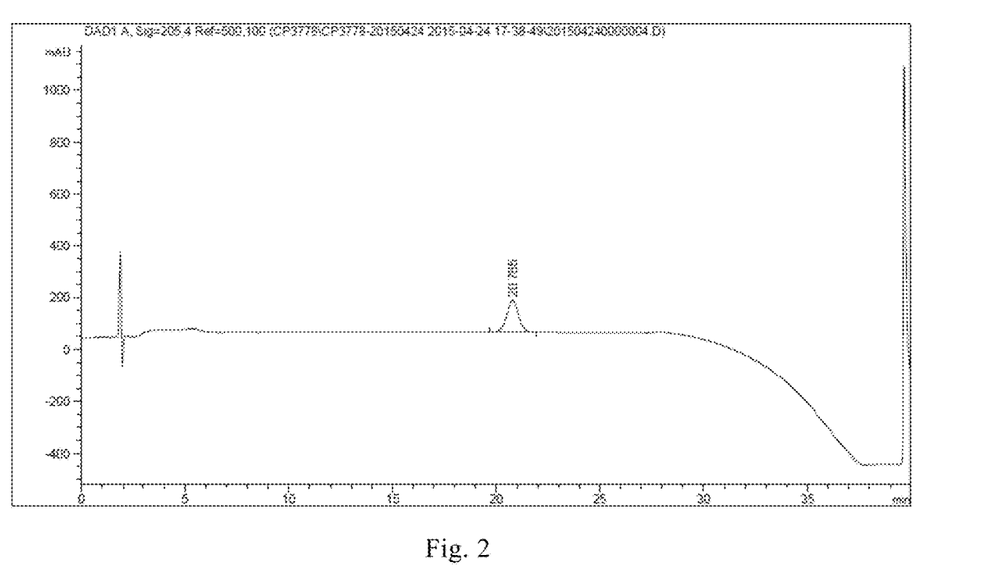
FIG. 2 shows the HPLC of the maleate of the compound of formula (I)

A high purity was observed of maleate (Table 7 and FIG. 2).

TABLE 7

HPLC impurity table of maleate

| # Peak | Time (min) | RRT | Area (%) |
|---|---|---|---|
| 1 | 20.78 | 1.00 | 100.00 |

Example 4: Preparation and Characterization of Salt Hits

Figure 1:
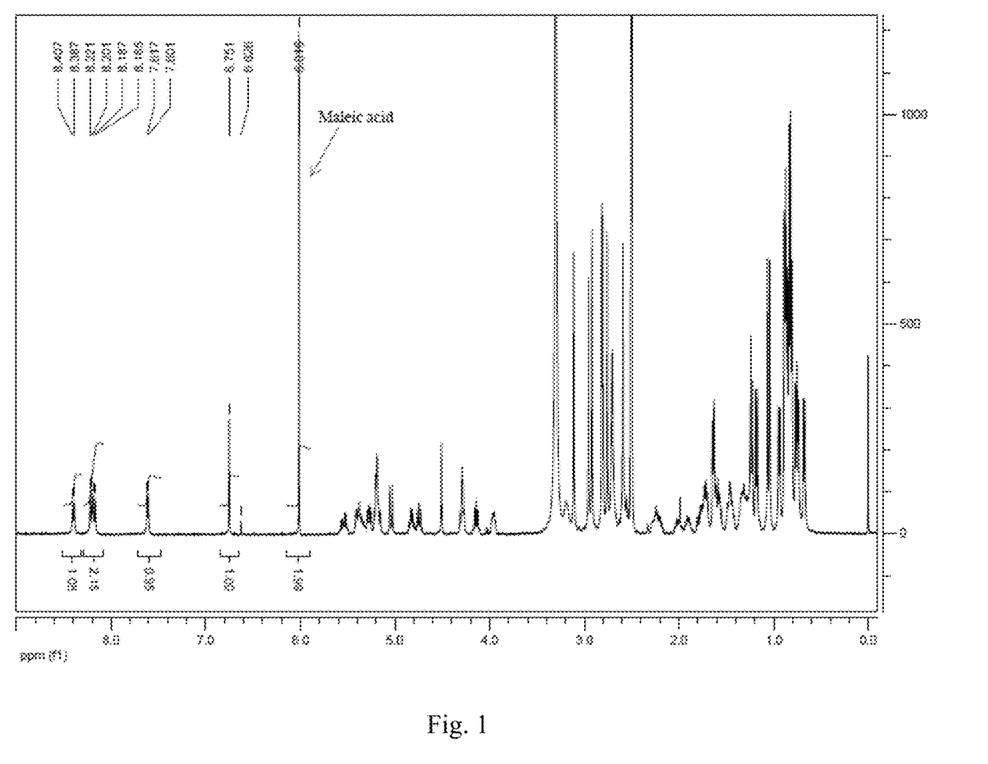
FIG. 1 shows the $^1$H NMR of the maleate of the compound of formula (I)
Figure 3:
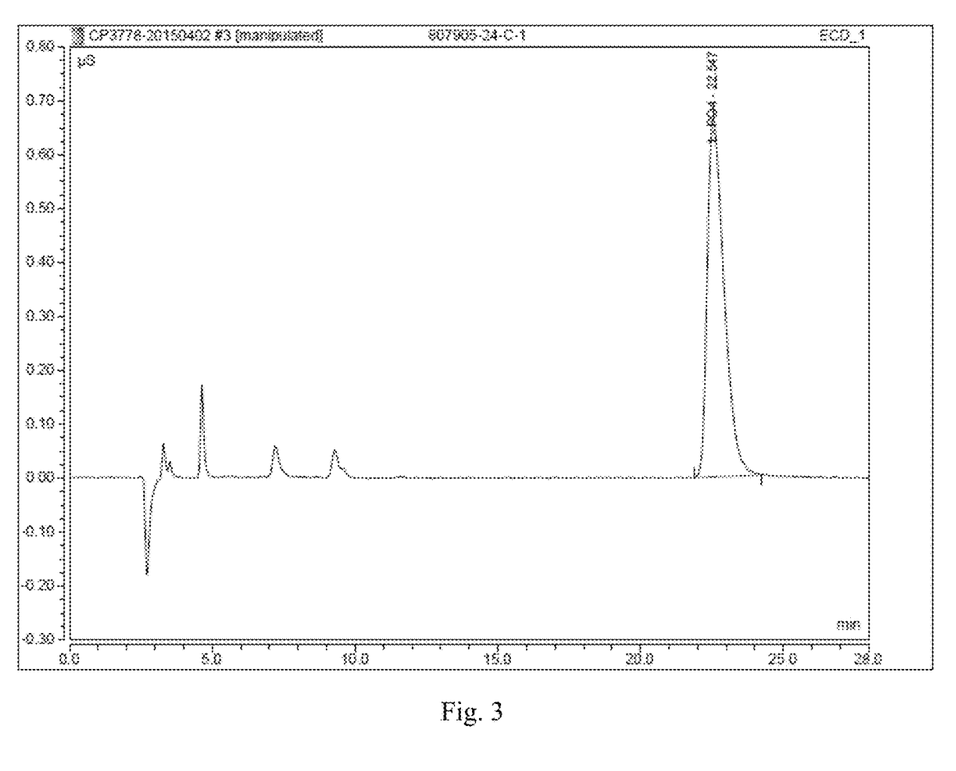
FIG. 3 shows the Ion chromatogram (IC) of the phosphate of the compound of formula (I)
Figure 4:
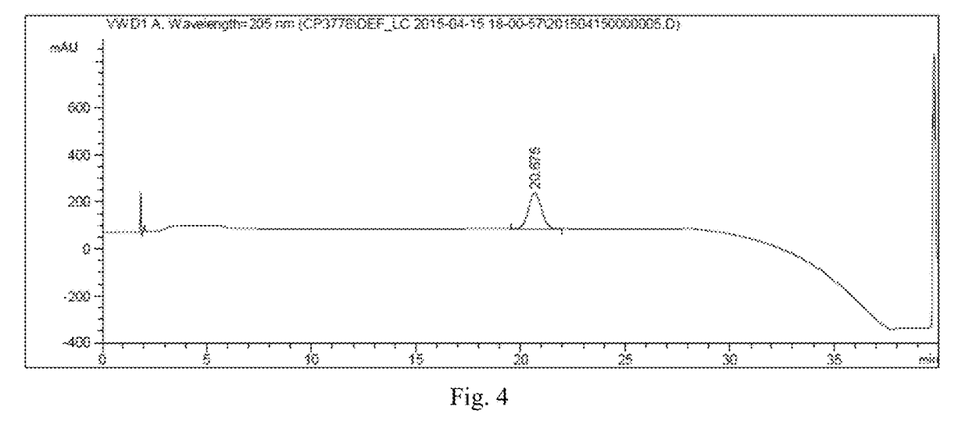
FIG. 4 shows the HPLC of the phosphate of the compound of formula (I)
Figure 5:
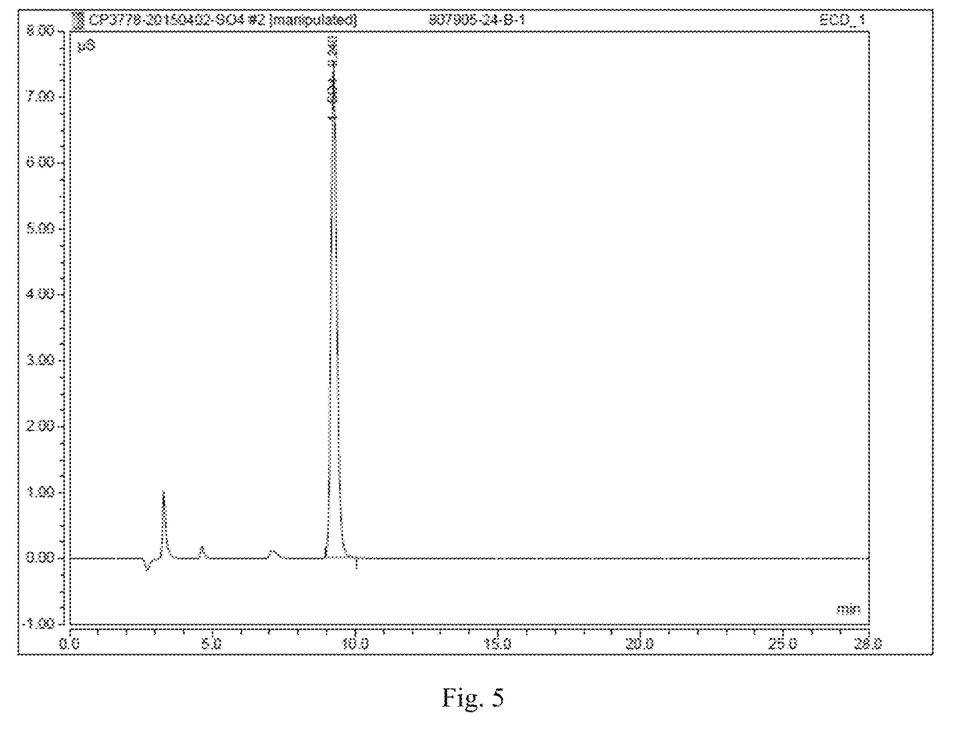
FIG. 5 shows the Ion chromatogram (IC) of the sulfate of the compound of formula (I)
Figure 6:
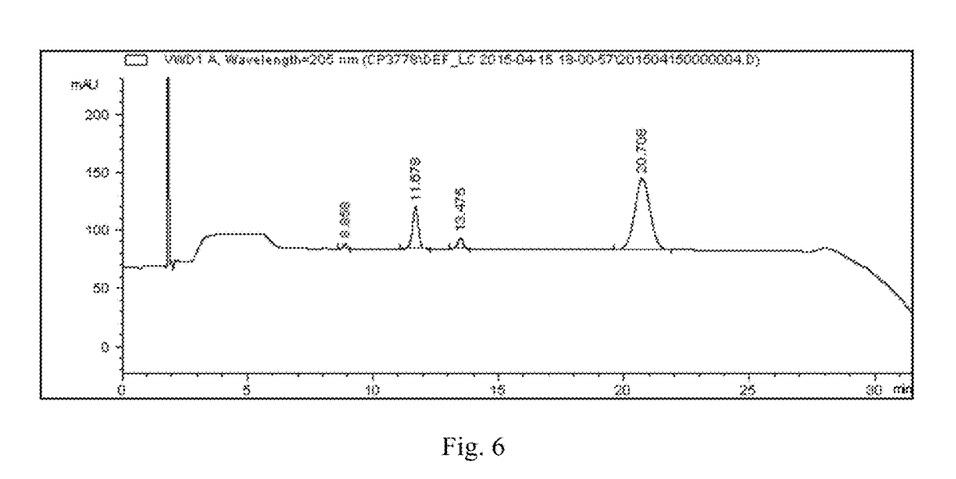
FIG. 6 shows the HPLC of the sulfate of the compound of formula (I)
Figure 7:
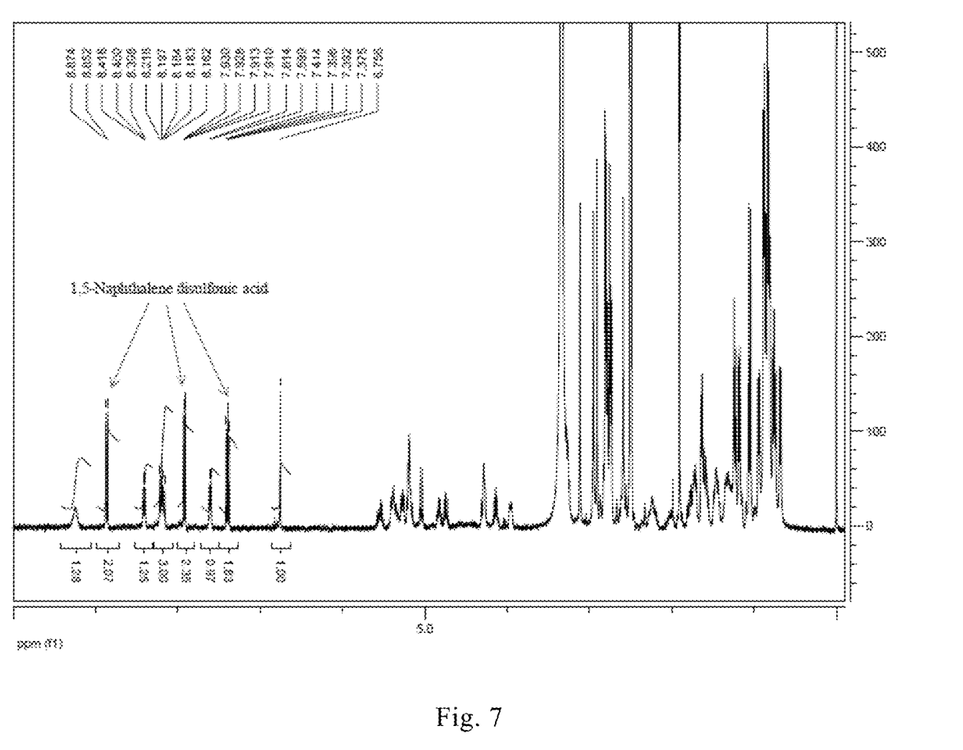
FIG. 7 shows the $^1$H NMR of the napadisylate of the compound of formula (I)

As characterized by $^1$H NMR and IC, four amorphous salts including maleate, napadisylate, sulfate and phosphate were formed. FIG. 1 shows the $^1$H NMR (DMSO-d6) of the maleate of the compound of formula (I), FIG. 3 shows the Ion chromatogram (IC) of the phosphate of the compound of formula (I), FIG. 5 shows the Ion chromatogram (IC) of the sulfate of the compound of formula (I), FIG. 7 shows the $^1$H NMR (DMSO-d6) of the napadisylate of the compound of formula (I). As the results, amorphous sulfate and phosphate were successfully re-prepared with the properties summarized in Table 8.

TABLE 8

Properties summary of salt hits

| Salt Hit | Maleate | Phosphate | Sulfate | Napadisylate |
|---|---|---|---|---|
| Scale | 200 mg | 50 mg | 50 mg | 20 mg |
| Crystallinity | Crystalline | Amorphous | Amorphous | Amorphous |
| HPLC purity | High purity | High purity | Low purity (77%) | N/A |
| Stoichiometry (acid/freebase) | 1.0 | 1.0* | 1.4 | 0.8 |

**Different stoichiometries detected for samples from various batches. N/A: Not determined.

Experimental results showed that only maleate, napadisylate, sulfate and phosphate were formed, and the said four salts of SCY-635 showed better solubility and stability than SCY-635 itself. Meanwhile, maleate showed the highest purity, consistent stoichiometric ratio between batches and minor residual EtOAc among the said four salts of SCY-635, which can be chosen as a leading salt for further evaluation.

Figure 8:
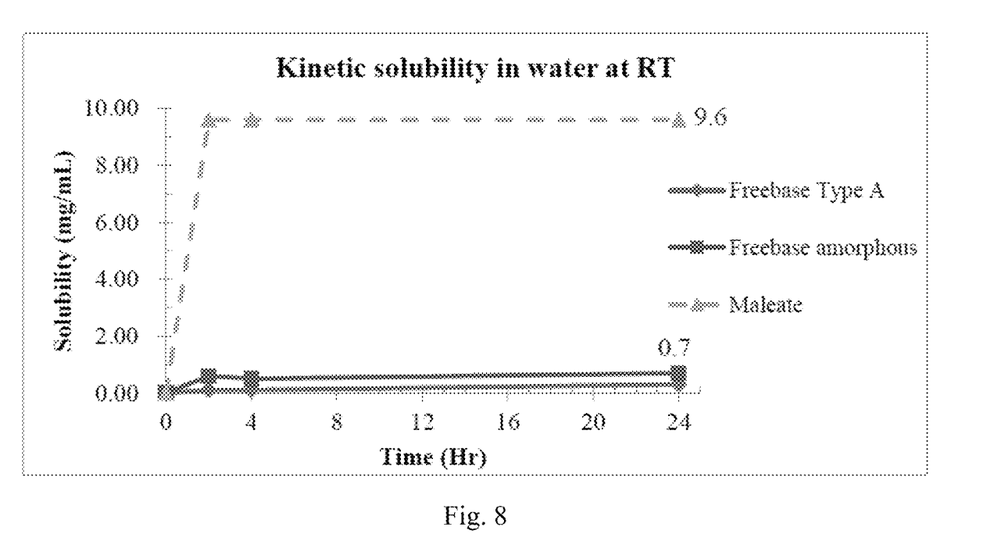
FIG. 8 shows the kinetic solubility profile in water at RT.
Figure 9:
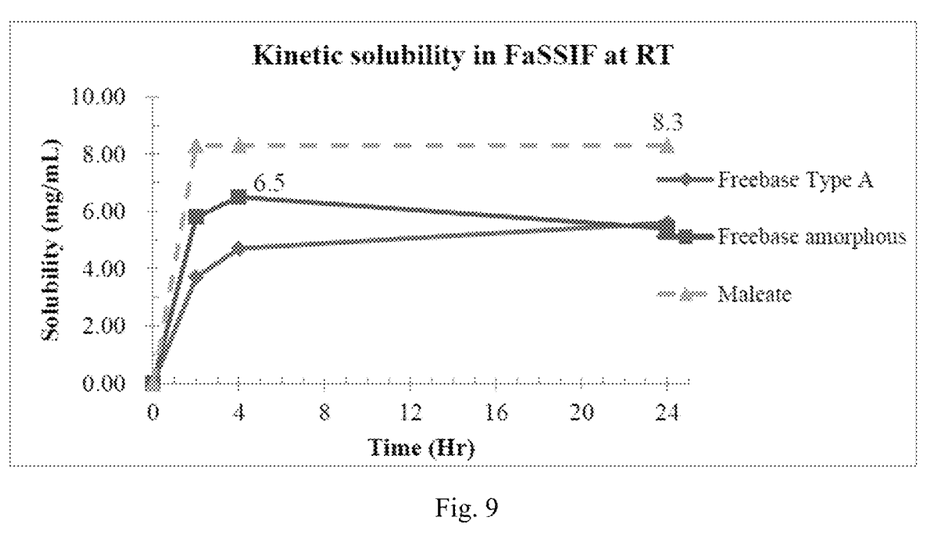
FIG. 9 shows the kinetic solubility profile in FaSSIF at RT.

Crystalline maleate was recommended as a leading salt and further evaluated by kinetic solubility and physicochemical stability. As results showed, significant solubility improvement was observed in water and FaSSIF compared with that of both amorphous and crystalline freebase (as shown in FIG. 8~9 and Table 9~10), and good chemical stability was proved under both 25° C./60% RH and 40° C./75% RH conditions for at least one week (as shown in Table 11).

TABLE 9

Kinetic Solubility in Water at RT

| | 2 hrs | | | 4 hrs | | | 6 hrs | | |
|---|---|---|---|---|---|---|---|---|---|
| Solid Form | $S^1$ | $pH^2$ | $FC^3$ | $S^1$ | $pH^2$ | $FC^3$ | $S^1$ | $pH^2$ | $FC^3$ |
| Freebase Type A | 0.1 | 6.7 | N | 0.1 | 6.5 | N | 0.3 | 6.6 | N |
| Freebase amorphous | 0.6 | 4.9 | N | 0.5 | 4.7 | N | 0.7 | 6.2 | N |
| Maleate | Clear | N/A | N/A | Clear | N/A | N/A | ≥9.6 | 4.9 | N/A |

TABLE 10

Kinetic Solubility in FaSSIF at RT

| | 2 hrs | | | 4 hrs | | | 6 hrs | | |
|---|---|---|---|---|---|---|---|---|---|
| Solid Form | $S^1$ | $pH^2$ | $FC^3$ | $S^1$ | $pH^2$ | $FC^3$ | $S^1$ | $pH^2$ | $FC^3$ |
| Freebase Type A | 3.7 | 6.8 | N | 4.7 | 6.8 | N | 5.6 | 7.0 | N |
| Freebase amorphous | 5.8 | 6.9 | N | 6.5 | 6.9 | N | 5.4 | 7.0 | N |
| Maleate | Clear | N/A | N/A | Clear | N/A | N/A | ≥8.3 | 6.0 | N/A |

[1]Solubility in mg/mL,
[2]Final pH of supernatant,
[3]Solid form change measured using XRPD.
N/A: No data available.

As results showed in Table 9~10, compared with both crystalline freebase and amorphous freebase, maleate showed improved solubility in water (≥9.6 mg/mL) and FaSSIF (≥8.3 mg/mL).

Physicochemical stability of crystalline maleate was evaluated under 25° C./60% RH-open and 40° C./75% RH-open for one week.

TABLE 11

One-week stability evaluation of maleate

| Condition | Purity (area%) | Purity of initial (%) |
|---|---|---|
| Initial | 100.0 | — |
| 25° C./60% RH | 100.0 | 100.0 |
| 40° C./75% RH | 100.0 | 100.0 |

As results showed in Table 11, good chemical stability was showed under both selected conditions.

And in above embodiments, the XRPD data of the Freebase Type A was showed in Table 12.

TABLE 12

| Position [°2θ] | d-Interval [Å] | Relative intensity [%] | Position [°2θ] | d-Interval [Å] | Relative intensity [%] |
|---|---|---|---|---|---|
| 6.08 | 14.54 | 4.43 | 18.78 | 4.72 | 2.72 |
| 8.66 | 10.21 | 100.00 | 19.38 | 4.58 | 1.56 |

TABLE 12-continued

| Position [°2θ] | d-Interval [Å] | Relative intensity [%] | Position [°2θ] | d-Interval [Å] | Relative intensity [%] |
|---|---|---|---|---|---|
| 9.64 | 9.18 | 8.91 | 20.40 | 4.35 | 7.25 |
| 10.36 | 8.54 | 18.44 | 21.71 | 4.09 | 1.98 |
| 11.20 | 7.90 | 16.22 | 22.04 | 4.03 | 5.20 |
| 12.58 | 7.04 | 3.44 | 22.49 | 3.95 | 2.18 |
| 13.00 | 6.81 | 4.68 | 23.20 | 3.83 | 0.98 |
| 13.58 | 6.52 | 1.32 | 23.88 | 3.73 | 0.90 |
| 14.14 | 6.26 | 6.77 | 24.99 | 3.56 | 1.62 |
| 14.90 | 5.95 | 5.56 | 25.82 | 3.45 | 0.75 |
| 15.36 | 5.77 | 2.94 | 26.77 | 3.33 | 1.13 |
| 15.98 | 5.55 | 2.39 | 27.61 | 3.23 | 0.99 |
| 16.71 | 5.30 | 2.65 | 28.43 | 3.14 | 0.93 |
| 17.69 | 5.01 | 2.72 | 29.62 | 3.02 | 0.89 |
| 18.39 | 4.82 | 10.06 | 31.36 | 2.85 | 0.56 |

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

What is claimed is:

1. A salt of a compound of formula (I):

wherein the salt is maleate.

2. The salt of claim 1, wherein a mole ratio of the compound of formula (I) to maleic acid in the maleate of the compound of formula (I) is from 1:0.9 to 1.1.2.

3. The salt of claim 1, wherein a mole ratio of the compound of formula (I) to maleic acid in the maleate of the compound of formula (I) is 1:1.

4. A pharmaceutical composition comprising the salt of claim 1, and a pharmaceutically acceptable excipient.

5. A method of preventing, managing, treating or lessening chronic hepatitis C and hepatitis C infection, comprising administering to a patent in need of such treatment a therapeutically effective amount of the salt of claim 1.

* * * * *